US005632883A

United States Patent [19]

Hoetzel

[11] Patent Number: 5,632,883

[45] Date of Patent: May 27, 1997

[54] METHOD AND A DEVICE FOR DETECTING THE OXYGEN CONTENT IN GASES

[75] Inventor: Gerhard Hoetzel, Stuttgart, Germany

[73] Assignee: Robert Bosch GmbH, Stuttgart, Germany

[21] Appl. No.: 545,848

[22] PCT Filed: Feb. 28, 1995

[86] PCT No.: PCT/DE95/00258

§ 371 Date: Nov. 13, 1995

§ 102(e) Date: Nov. 13, 1995

[87] PCT Pub. No.: WO95/24643

PCT Pub. Date: Sep. 14, 1995

[30] Foreign Application Priority Data

Mar. 10, 1994 [DE] Germany .......................... 44 08 021.2

[51] Int. Cl.[6] .................................................. G01N 27/407

[52] U.S. Cl. ....................... 205/784.5; 204/424; 204/425; 204/426; 204/427

[58] Field of Search .................................... 204/421–429; 205/783.5, 784, 784.5, 785

[56] References Cited

U.S. PATENT DOCUMENTS

| | | | |
|---|---|---|---|
| 4,207,159 | 6/1980 | Kimura et al. . | |
| 4,231,733 | 11/1980 | Hickam et al. | 204/426 |
| 4,298,573 | 11/1981 | Fujishiro | 204/425 |
| 4,384,935 | 5/1983 | De Jong | 204/425 |
| 4,853,091 | 8/1989 | Mund et al. | 204/402 |

FOREIGN PATENT DOCUMENTS

| | | |
|---|---|---|
| 0035177 | 9/1981 | European Pat. Off. . |
| 0082372 | 6/1983 | European Pat. Off. . |
| 0140295 | 5/1985 | European Pat. Off. . |
| 0145073 | 6/1985 | European Pat. Off. . |
| 0168938 | 1/1986 | European Pat. Off. . |
| 2050625 | 1/1981 | United Kingdom . |
| 2219093 | 11/1989 | United Kingdom . |
| 2276458 | 9/1994 | United Kingdom . |

*Primary Examiner*—T. Tung

*Attorney, Agent, or Firm*—Walter Ottesen

[57] ABSTRACT

The invention relates to a device for detecting the oxygen content in a gas to be measured, wherein the device comprises at least one concentration cell which includes a measuring electrode, a solid electrolyte and a reference electrode. The measuring electrode communicates with the gas to be measured and is connected via the solid electrolyte to the reference electrode, which communicates with a reference gas volume. The reference gas volume is separated from the gas to be measured in such a way that a particle exchange between the reference gas volume and the gas to be measured is at least impeded. The output voltage of the concentration cell, which voltage can be tapped off between the measuring electrode and the reference electrode, represents a measure of the difference in the oxygen concentrations in the gas to be measured and in the reference gas volume. The device further comprises a current source which can be coupled in between the reference electrode and the measuring electrode in such a way that in the coupled-in state a current flow results which is directed such that oxygen is transported in the solid electrolyte from the measuring electrode to the reference electrode. The device further comprises switching means which, in a first switching state, couples the current source to the concentration cell and which, in a second switching state, decouples the current source from the concentration cell, so that the voltage between the measuring electrode and the reference electrode in the decoupled state is not affected by the current source.

3 Claims, 1 Drawing Sheet

Exhaust gas

Air 1 3 4 2 9 10 12 7 8 S 5 6 11

O $I_p$

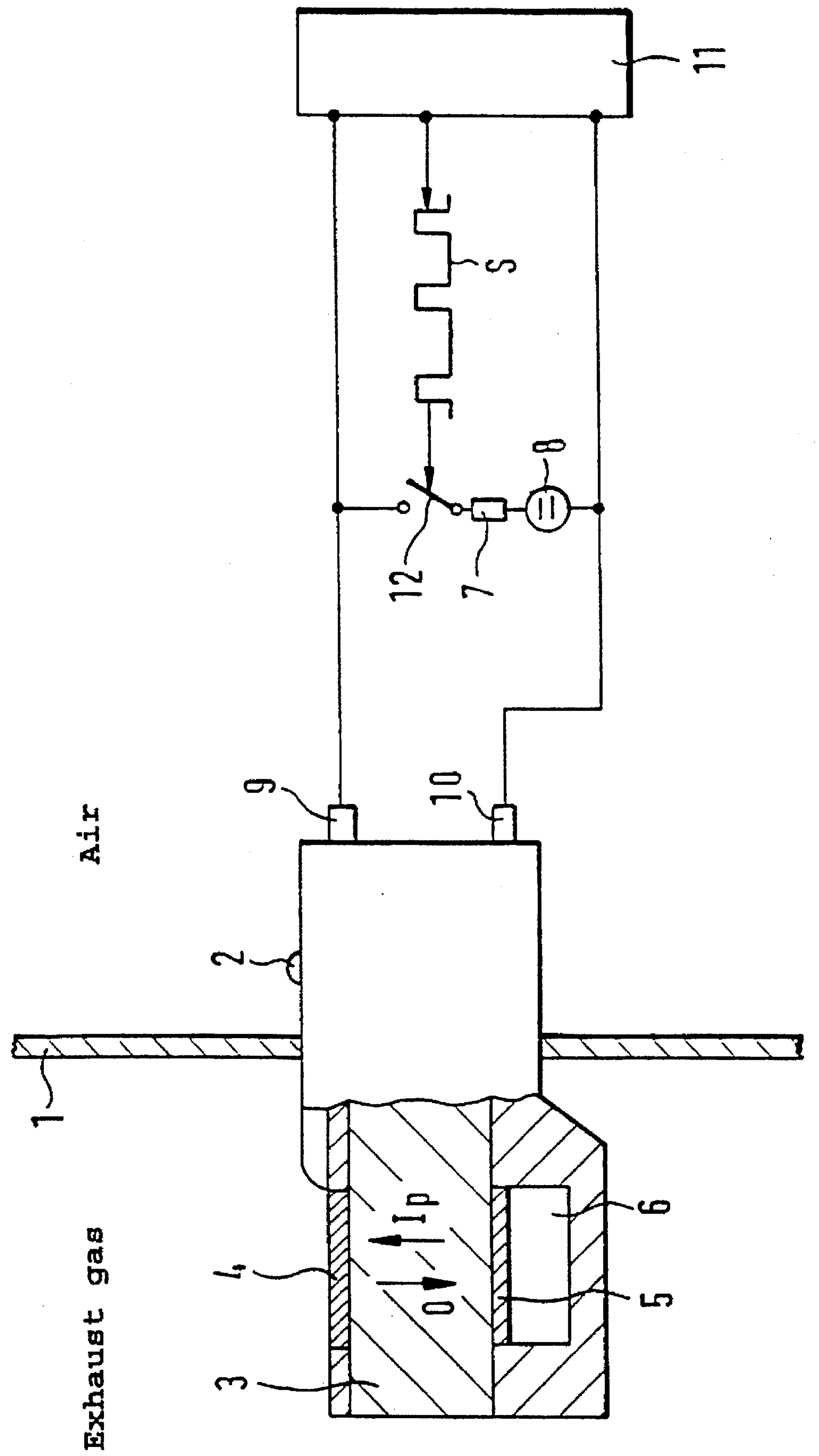
11
S
8
12
7
9
10
Air
2
1
Exhaust gas
4
3
Ip
O
6
5

METHOD AND A DEVICE FOR DETECTING THE OXYGEN CONTENT IN GASES

STATE OF THE ART

1. Field of the Invention

The invention relates to a device for detecting the oxygen content in gases, for example, in the exhaust gas of an internal combustion engine.

2. Background of the Invention

It is known to measure the oxygen content of exhaust gases with the aid of a concentration cell, for example made of $ZrO_2$ ceramic, against the reference oxygen content in a reference atmosphere. The reference atmosphere can be defined, for example, by the ambient air or alternatively by a reference gas in a space which is sealed off or virtually sealed off with respect to the ambient. In the case of different oxygen partial pressures in the exhaust gas and the reference gas, the cell generates an electromotive force Un which, in accordance with the Nernst equation, depends on the logarithm of the quotient of the oxygen partial pressures. If the reference gas composition is known, Un can be tapped off from the cell via measuring electrodes and can be used as a measure of the oxygen content of the exhaust gas. In conjunction with a limited reference gas volume, the problem arises that the composition of the reference gas can change. Diffusion processes result, for example, in equalization of the oxygen concentrations thereby causing Un to vanish. To overcome this problem, it is known, for example, from U.S. Pat. No. 4,207,159, to impress a pump current Ip onto the concentration cell with the aid of a constant current source via the measuring electrode. The pump current Ip is so directed that the reference gas volume is continuously supplied with oxygen from the exhaust gas. Thus it is possible, on the one hand, to maintain a difference in the oxygen partial pressures. On the other hand, this pump current Ip leads, in conjunction with the electrical resistance Ri of the electrolyte and of the electrodes, to a voltage drop Ri*Ip which superimposes itself additively on the electromotive force Un of the cell to provide a total signal Un+Ri*Ip.

SUMMARY OF THE INVENTION

It is the object of the invention to provide a method and a device by means of which the additive offset Ri*Ip is eliminated. This additive offset Ri*Ip represents a disturbance of the useful signal Un because of the temperature dependence of the resistance Ri.

The invention achieves this object by providing a device for detecting the oxygen content in a gas to be measured. The device has at least one concentration cell which operates according to the Nernst principle and includes a measuring electrode, a solid electrolyte and a reference electrode. The measuring electrode communicates with the gas to be measured and is connected via the solid electrolyte to the reference electrode, which communicates with the reference gas volume. The reference gas volume is separated from the gas to be measured in such a way that a particle exchange between the reference gas volume and the gas to be measured is at least impeded. The output voltage of the concentration cell, which voltage can be tapped off between the measuring electrode and the reference electrode, represents a measure of the difference in the oxygen concentrations in the gas to be measured and in the reference gas volume. The device further comprises a current source which is coupled in between the reference electrode and the measuring electrode in such a way that, in the coupled-in state, a current flow results which is directed such that oxygen is transported in the solid electrolyte from the measuring electrode to the reference electrode. The device further comprises switching means which, in a first switching state, couples the current source to the concentration cell and which, in a second switching state, decouples the current source from the concentration cell so that the voltage between the measuring electrode and the reference electrode in the decoupled state is not affected by the current source.

A corresponding method for detecting the oxygen content in gases to be measured with the aid of the above-mentioned device is characterized in that a variable, which is characteristic of the voltage between the measuring electrode and the reference electrode, is used for detecting the oxygen content in those situations where the switching means is in the second switching state.

In this way, the temperature-dependent effect of the pump current on the voltage, which can be tapped off between the gas to be measured and the reference gas, is avoided so that a complex temperature control of the concentration cell is unnecessary.

BRIEF DESCRIPTION OF THE DRAWING

The invention will now be described with respect to the single FIGURE of the drawing which shows an embodiment of the device of the invention for detecting the oxygen content in the exhaust gas of an internal combustion engine such as utilized as a power source for motor vehicles.

DESCRIPTION OF THE PREFERRED EMBODIMENT OF THE INVENTION

The drawing shows a section view of an exhaust-gas probe 2 in an exhaust-gas pipe of which a wall 1 is shown. This wall separates the exhaust gas of an internal combustion engine (to the left) from the ambient air (to the right). The exhaust-gas probe contains, in its portion facing the exhaust gas, a solid electrolyte 3 between a measuring electrode 4 exposed to the exhaust gas and a reference electrode 5. A reference gas volume 6 communicating with the measuring electrode 4 is neither in direct contact with the exhaust gas nor with the ambient air. Any overpressure which may build up in the reference gas volume is reduced via an indirect connection to the ambient air, for example, via a measuring input line 10 of porous configuration. The input line 10 is connected to the reference electrode and an input line 9 is connected to the measuring electrode. Between these two lines (9, 10), a current source is connected which comprises a direct-current voltage source 8 (Uv) and a series resistor 7 (Rv) via a switching means 12. This configuration is intended only as an embodiment of a pump current source. Alteratively, the pump current can be generated in any other way, for example, by means of a constant-current source. Depending on the switching state of the switching means 12, the voltage US between the measuring electrode and the reference electrode is made up of different components. In the case of a nonconducting switching means, US is equal to the Nernst voltage Un of the concentration cell, and in the case of a conducting switching means, US=Un+Ri*Ip, wherein Ip represents the pump current supplied to by the current source and Ri represents the internal resistance of the concentration cell.

The switching means 12 can be realized, for example, by a transistor switch which is alternately driven from the conducting into the nonconducting state by the control apparatus 11 by means of a signal S.

In the nonconducting state, the signal US=Un is independent of the temperature-dependent offset Ri*Ip and can be used as a measure of the oxygen content of the exhaust gas, for example for mixture control.

In order-to maintain a stable reference gas atmosphere, it is essential that, averaged over time, the oxygen supply via the pump current Ip exceeds the oxygen losses. Such losses inevitably occur for a nonconducting means 12 because of the measurement of the voltage US=Un when the voltage measurement is reduced to a current measurement via a measuring shunt. In the context of measuring voltages in the order of magnitude of an output voltage Un of an exhaust-gas probe of one volt, measuring shunts in the megaohm range are typically used. Consequently a measured current will be in the microampere range. In the electrolyte, this current is supported by oxygen ions from the reference gas volume, so that the oxygen concentration in the reference gas volume decreases as a result of the measurement.

In order to keep any influence of this effect on the emf of the concentration cell to a minute level, it was found to be advantageous, for reference gas volumes such as are used in the field of exhaust gas probes for motor vehicles, to limit the measuring time to values between 50 and 150 ms and to use approximately one tenth of this time for feeding in the pump current Ip. On the assumption, for example, of a measuring time of 100 ms for a measurement current of one microampere, the electrical charge corresponding to the product of these variables, which is transported by oxygen ions from the reference gas volume, has to be replaced by the pump current Ip. In the context of the conditions selected in the present case, this requires a pump current of at least 10 microamperes. In order to ensure a stable reference gas composition it makes sense to increase this minimum pump current by a factor of 2 to 3. Instead of one tenth of the measuring time, a value for the pump time of from one twentieth to half the measuring time may be advantageous.

I claim:

1. A device for detecting the oxygen content in the exhaust gas of an internal combustion engine, the device comprising:

a concentration measuring cell operating pursuant to the Nernst principle and including:

a solid electrolyte;

a measuring electrode arranged on said solid electrolyte and exposed to said exhaust gas, said exhaust gas containing gas particles;

a reference electrode arranged on said electrolyte and being connected to said measuring electrode through said solid electrolyte;

said solid electrolyte including holding means for holding a volume of reference gas separated from ambient air and in contact with said reference electrode and said reference gas containing gas particles;

means for separating said reference gas volume from said exhaust gas containing gas particles so that an exchange of particles between said reference gas volume and said exhaust gas is impeded; and, said concentration measuring cell having an output voltage across said measuring and reference electrodes and said output voltage defining a measure for the difference of the oxygen concentration in said exhaust gas and said reference gas volume; and, said device further including:

a current source for supplying a pump current having a predetermined magnitude;

switching means connected to said current source and being switchable between a first position for a first duration wherein said current source is connected between said measuring and reference electrodes to provide a flow of said pump current directed to cause oxygen to be transported in said solid electrolyte from said measuring electrode to said reference electrode and a second position for a second duration wherein said current source is disconnected from said concentration measuring cell and said pump current is interrupted whereby said output voltage between said measuring and reference electrodes is unaffected by said current source;

said first and second time durations defining a time ratio; and, a control apparatus for generating a switching signal for driving said switching means between said first and second positions and said control apparatus including means for selecting said time ratio and said magnitude of said pump current so that the flow of oxygen to said reference gas volume during said first time duration exceeds, in time average, a flow of oxygen out of said reference gas volume during said second time duration.

2. A method for detecting the oxygen content in the exhaust gas of an internal combustion engine utilizing a device which includes a concentration measuring cell operating pursuant to the Nernst principle and including: a solid electrolyte; a measuring electrode arranged on said solid electrolyte and exposed to said exhaust gas, said exhaust gas containing gas particles; a reference electrode arranged on said electrolyte and being connected to said measuring electrode through said solid electrolyte; said solid electrolyte including holding means for holding a volume of reference gas separated from ambient air and in contact with said reference electrode and said reference gas containing gas particles; means for separating said reference gas volume from said exhaust gas containing gas particles so that an exchange of particles between said reference gas volume and said exhaust gas is impeded; and, said concentration measuring cell having an output voltage across said measuring and reference electrodes and said output voltage defining a measure for the difference of the oxygen concentration in said exhaust gas and said reference gas volume; and, the device further including a current source for supplying a pump current having a predetermined magnitude; switching means connected to said current source and being switchable between a first position wherein said current source is connected between said measuring and reference electrodes to provide a current flow directed to cause oxygen to be transported in said solid electrolyte from said measuring electrode to said reference electrode and a second position wherein said current source is disconnected from said concentration cell and said pump current is interrupted whereby said output voltage between said measuring and reference electrodes is unaffected by said current source; the method comprising the steps of:

effecting the first position of the switch means for a first time duration to cause oxygen to be transported to the reference electrode;

effecting the second position of the switch means for a second time duration to disconnect the current source from the electrodes with said first and second time durations defining a time ratio;

measuring the voltage between the electrodes as an indication of the oxygen content in the exhaust gas while the current source is disconnected; and, selecting said time ratio and said magnitudes of said pump current so that the flow of oxygen to said reference gas volume during said first time duration exceeds, in time average, a flow of oxygen out of said reference gas volume during said second time duration.

3. The method of claim 2, said first time duration being from 0.05 to 0.5 of said second time duration.

* * * * *